US012383043B2

(12) United States Patent
Chan et al.

(10) Patent No.: US 12,383,043 B2
(45) Date of Patent: Aug. 12, 2025

(54) ORAL APPLIANCE HOLDER

(71) Applicant: Smylio Inc., Fremont, CA (US)

(72) Inventors: Henry Hanh Chan, San Jose, CA (US); Irene Vincenza Laudeman, Boise, ID (US)

(73) Assignee: Smylio Inc., Fremont, CA (US)

( * ) Notice: Subject to any disclaimer, the term of this patent is extended or adjusted under 35 U.S.C. 154(b) by 340 days.

(21) Appl. No.: 17/607,277

(22) PCT Filed: Apr. 29, 2020

(86) PCT No.: PCT/US2020/030519
§ 371 (c)(1),
(2) Date: Oct. 28, 2021

(87) PCT Pub. No.: WO2020/223380
PCT Pub. Date: Nov. 5, 2020

(65) Prior Publication Data
US 2022/0202169 A1 Jun. 30, 2022

Related U.S. Application Data

(60) Provisional application No. 62/840,613, filed on Apr. 30, 2019.

(51) Int. Cl.
*A45D 44/20* (2006.01)
*A61C 19/02* (2006.01)
(Continued)

(52) U.S. Cl.
CPC ............. *A45D 44/20* (2013.01); *A61C 19/02* (2013.01); *A61L 2/24* (2013.01); *A61L 2/26* (2013.01);
(Continued)

(58) Field of Classification Search
CPC .......... A45D 44/20; A61C 19/02; A61C 7/08; A61L 2/24; A61L 2/26; A61L 2202/14; B65D 25/10; B65D 43/16; G16H 10/60
See application file for complete search history.

(56) References Cited

U.S. PATENT DOCUMENTS 6,244,096 B1   6/2001  Lewis et al.
6,417,761 B1   7/2002  Elliott
(Continued)

FOREIGN PATENT DOCUMENTS

DE   102005056293 A1   5/2007
EA        024907 B1    11/2016
(Continued)

OTHER PUBLICATIONS

Delval, C., Supplemental Partial European Search Report for European Patent Appl. No. 20799038.3, Dec. 13, 2022.
(Continued)

*Primary Examiner* — Mohamed Barakat
(74) *Attorney, Agent, or Firm* — MT HUNT LAW; Marcus T. Hunt

(57) ABSTRACT

In certain aspects, devices and methods for an oral appliance holder that can detect analyte information originating from oral appliances stored in the appliance holder. The analyte information can be derived from found in volatilized compounds detected within the appliance holder. The appliance holder can directly or indirectly communicate with a server that is configured to process the analyte information. The analyte information can be processed to develop a wellness profile.

17 Claims, 8 Drawing Sheets

(51) Int. Cl.
    *A61L 2/24* (2006.01)
    *A61L 2/26* (2006.01)
    *B65D 25/10* (2006.01)
    *B65D 43/16* (2006.01)
    *G16H 10/60* (2018.01)
    *A61C 7/08* (2006.01)

(52) U.S. Cl.
    CPC ............ *B65D 25/10* (2013.01); *B65D 43/16* (2013.01); *G16H 10/60* (2018.01); *A61C 7/08* (2013.01); *A61L 2202/14* (2013.01)

(56) References Cited

U.S. PATENT DOCUMENTS

| | | |
|---|---|---|
| 6,575,013 B2 | 6/2003 | Bao et al. |
| 7,531,137 B2 | 5/2009 | Uluyol |
| 7,748,199 B2 | 7/2010 | Sankaran et al. |
| 7,977,103 B2 | 7/2011 | Martin et al. |
| 8,030,588 B2 | 10/2011 | Culp et al. |
| 8,366,630 B2 | 2/2013 | Haick et al. |
| 8,383,977 B2 | 2/2013 | Culp et al. |
| 8,438,817 B2 | 5/2013 | Sankaran et al. |
| 9,152,145 B2 | 10/2015 | Culp et al. |
| 9,522,750 B2 | 12/2016 | Sankaran et al. |
| 9,733,226 B1 | 8/2017 | Lowy |
| 9,980,799 B2 | 5/2018 | Wilson |
| 10,099,256 B2 | 10/2018 | Culp et al. |
| 10,501,214 B2 | 12/2019 | Sankaran et al. |
| 10,588,728 B2 | 3/2020 | Wilson |
| 11,464,612 B2 | 10/2022 | Wilson et al. |
| 11,638,535 B2* | 5/2023 | Weinstein ............ G01N 27/414 433/27 |
| 2004/0142495 A1 | 6/2004 | Hartman et al. |
| 2004/0147038 A1 | 7/2004 | Lewis et al. |
| 2004/0236244 A1 | 11/2004 | Allen et al. |
| 2005/0171449 A1 | 8/2005 | Suslick et al. |
| 2005/0208614 A1 | 9/2005 | Kline et al. |
| 2007/0028667 A1* | 2/2007 | Kim ................... G01N 33/0031 29/595 |
| 2009/0230300 A1 | 9/2009 | Trevejo et al. |
| 2009/0247890 A1 | 10/2009 | Hausmann et al. |
| 2010/0191474 A1 | 7/2010 | Haick |
| 2014/0263500 A1* | 9/2014 | Brooks ................... A61C 7/00 224/269 |
| 2014/0271948 A1* | 9/2014 | LoPesio ................ A01N 65/00 424/736 |
| 2015/0105683 A1 | 4/2015 | Bos |
| 2015/0313354 A1* | 11/2015 | Mongan ................... A61L 2/24 15/105 |
| 2017/0008333 A1* | 1/2017 | Mason ................... B44C 1/228 |
| 2017/0337347 A1 | 11/2017 | Chu |
| 2018/0014380 A1* | 1/2018 | Kornicki ............. A61C 17/036 |
| 2018/0368961 A1 | 12/2018 | Shanjani et al. |
| 2019/0039100 A1 | 2/2019 | Culp et al. |
| 2019/0069975 A1* | 3/2019 | Cam ................... A61B 5/4833 |
| 2019/0110746 A1* | 4/2019 | Dau ......................... A61L 2/10 |
| 2020/0071006 A1 | 3/2020 | Sankaran et al. |
| 2021/0236052 A1* | 8/2021 | Wilson ................. A61B 5/4547 |

FOREIGN PATENT DOCUMENTS

| | | |
|---|---|---|
| EP | 2007286 A2 | 12/2008 |
| EP | 2215464 B1 | 10/2015 |
| KR | 1020100025599 A | 3/2010 |
| RU | 2481818 C1 | 5/2013 |
| RU | 2571280 C1 | 12/2015 |
| WO | 2003064994 A2 | 8/2003 |
| WO | 2005006981 A1 | 1/2005 |
| WO | 2008145322 A1 | 12/2008 |
| WO | 2009032410 A1 | 3/2009 |
| WO | 2009053981 A2 | 4/2009 |
| WO | 2009144725 A1 | 12/2009 |
| WO | 2012125734 A2 | 9/2012 |
| WO | 2012131386 A1 | 10/2012 |
| WO | 2017218947 A1 | 12/2017 |
| WO | 2019036677 A1 | 2/2019 |
| WO | 2019178247 A1 | 9/2019 |

OTHER PUBLICATIONS

Kuznetsova, Y., International Search Report & Written Opinion for PCT/US20/30519, Jul. 30, 2020.

Pamela Babcock; "Change Your Breath From Bad to Good"; retrieved on Sep. 16, 2024 from https://www.webmd.com/oral-health/change-your-breath-from-bad-to-good#1; 2 pages; Aug. 27, 2015.

* cited by examiner

ORAL APPLIANCE HOLDER

This application is a national stage application pursuant to 35 U.S.C. § 371 of International Application No. PCT/US20/30519, filed Apr. 29, 2020, which claims the benefit of U.S. Provisional Application No. 62/840,613, filed Apr. 30, 2019, and this application incorporates the aforementioned references herein.

FIELD OF THE INVENTION

The subject matter of the present disclosure relates generally to the field of oral appliances. More particularly, the present disclosure relates to devices for tracking patient wellness by detection of properties from the oral appliance.

BACKGROUND

An objective of orthodontics is to move a patient's teeth to positions where function and/or aesthetics are optimized. Traditionally, appliances such as braces are applied to a patient's teeth by a treating practitioner and the set of braces exerts continual force on the teeth and gradually urges them toward their intended positions. Over time and with a series of clinical visits and reactive adjustments to the braces by the practitioner, the appliances to move the teeth toward a desired destination. More recently, alternatives to conventional orthodontic treatment with traditional affixed appliances (e.g., braces) have become available. For example, systems including a series of molded plastic aligners have become commercially available from Align Technology, Inc., San Jose, Calif., under the trade name Invisalign® System. The Invisalign® System is described in numerous patents and patent applications assigned to Align Technology, Inc. including, for example in U.S. Pat. Nos. 6,450,807, and 5,975,893.

Like traditional braces, aligners are required to be worn near constant wear protocol (20-22 hours a day), with breaks allowed for eating and cleaning teeth. Patient compliance with the wear protocol is greatly determinative of a successful orthodontic result. However, for various reasons, a certain number of patients do not comply with the wear protocol. This can result in a non-successful orthodontic result that requires a new series of aligners to be made or abandonment of the procedure. Compliance tracking devices exist, however they rely on simple sensors that are generally not capable of determining whether a current aligner is present or rather some other object, such as a prior aligner.

SUMMARY OF THE INVENTION

Some embodiments of the present disclosure relate to an aligner case having a compartment for housing electronics and a compartment for housing aligners. The electronics can detect the presence of the aligners and communicate with an external device, such as a smart phone, to provide appliance compliance information to a caregiver.

Some embodiments relate to a method for prescribing use of an oral appliance. In the method, time information generated by an oral appliance holder is received. The information can be related to detecting presence or non-presence of an oral appliance within the holder. The oral appliance can be one of a series of pre-designed oral appliances prescribed for oral treatment of a patient. It can be determined from the time information that the appliance was not present within the oral appliance holder for a required amount of time. The prescribed use of the series oral appliances can be altered based on the appliance not being present within the oral appliance holder for the required amount of time.

In some embodiments, accessing can include accessing a remote server to download or view the information.

In some embodiments, altering the prescribed use of the series oral appliances can include changing an appliance currently used by the patient.

In some embodiments, altering the prescribed use of the series oral appliances can include changing reevaluating the patient for a new series of oral appliances.

In some embodiments, altering the prescribed use of the series oral appliances can include prescribing changing a currently prescribed oral appliance back to a prior oral appliance.

Some embodiments relate to a device for storing an oral appliance. The device can include an openable container. The openable container can have an appliance holding portion, a processor, a memory module coupled to the processor, a communication module, and a sensing module coupled to the appliance holding portion and the processor. The sensing module can be configured to generate to generate analyte information, the analyte information can be related to presence or non-presence of volatilized compounds emanating from an oral appliance at the appliance holding portion. The processor can be configured to receive the analyte information from the sensing module, generate and store use information within the memory module. The use information can include at least the analyte information. The communication module can transmit the use information to an external device.

Some embodiments relate to a method in which analyte information can be received from a sensing module of an oral appliance holder, the analyte information can be related to presence or non-presence of an oral appliance at the appliance holding portion of the oral appliance holder. Use information can be generated and stored at a memory module of the oral appliance holder. The use information can include at least the analyte information. A communication module of the oral appliance holder can be connected to an external device. The use information can be transmitted from the oral appliance holder to an external device.

Some embodiments relate to a non-transitory processor-readable medium for an oral appliance holder, the non-transitory processor-readable medium can include processor-readable instructions configured to cause one or more processors of the oral appliance holder to perform a method in which analyte information can be received from a sensing module of the oral appliance holder. The analyte information can be related to presence or non-presence of an oral appliance at the appliance holding portion of the oral appliance holder. Use information can be generated and stored at a memory module of the oral appliance holder. The use information can include at least the analyte information. A communication module of the oral appliance holder can be connected to an external device. The use information can be transmitted from the oral appliance holder to an external device.

In some embodiments, the volatilized compounds comprise one or more of alkanes, alkenes, alkynes, dienes, alicyclic hydrocarbons, arenes, alcohols, ethers, ketones, aldehydes, carbonyls, carbanions, polynuclear aromatics, biomolecules, sugars, isoprenes isoprenoids, volatile organic compounds (VOC), volatile organic analytes (VOA), indoles, skatoles, diamines, pyridines, picolines, an off-gas of a microorganism and fatty acid, pentane, hydrogen sulfide, methyl mercaptan, ammonia, acetone, butane, and sulfides.

In some embodiments, the openable container can include a top lid at least partially removably connected to a bottom housing.

In some embodiments, at least one of the processor, memory module, communication module, and sensing module can be housed within the bottom housing.

In some embodiments, the communication module can be configured to wirelessly communicate with the external device.

In some embodiments, the external device is a smartphone or tablet.

In some embodiments, the sensing module can include at least one sensor.

In some embodiments, the at least one sensor can include at least one of an infra-red, piezo-electric, strain-gauge, hall-effect, capacitive, ultrasonic, microwave, radio, magnetic, humidity, or optical sensor.

In some embodiments, the external device can include a network access device.

In some embodiments, the network access device can be configured to transmit the use information to a remote server.

In some embodiments, a sanitizing module can be configured to sanitize the oral appliance at the appliance holding portion.

Some embodiments relate to a server that can have at least one processor. The at least one processor can be configured to perform a method in which a record can be received from a first external device. The record can include at least one, a single event, or multiple events that indicate the presence or non-presence of an oral appliance within an oral appliance holder. The events can include analyte information of volatilized compounds emanating from the oral appliance. The record can be correlated with a patient's master record. The patient's master record can be updated to include the record. Remote access to the patient's master record by a second external device can be enabled.

Some embodiments relate to a method in which a record can be received from a first external device. The record can include a single event or multiple events that indicate the presence or non-presence of an oral appliance within an oral appliance holder. The record can be correlated with a patient's master record. The patient's master record can be updated to include the record. Remote access to the patient's master record by a second external device can be enabled.

Some embodiments relate to a non-transitory processor-readable medium for a server. The non-transitory processor-readable medium can include processor-readable instructions configured to cause one or more processors of the server to perform a method in which a record can be received from a first external device. The record can include a single event or multiple events that indicate the presence or non-presence of an oral appliance within an oral appliance holder. The record can be correlated with a patient's master record. The patient's master record can be updated to include the record. Remote access to the patient's master record by a second external device can be enabled.

In some embodiments, the first external device can include a network access device communicatively couplable with the oral appliance holder.

In some embodiments, the analyte information can be correlated to at least one health attribute, bodily function, and/or wellness indicator.

In some embodiments, updating the patient's master record can include correlating analyte information with pre-existing information of the patient's master record to develop a statistically weighted model for the at least one health attribute, bodily function, and/or wellness indicator.

In some embodiments, the statistically based model can be a sub-profile of a plurality of sub-profiles that make up a health profile of the patient.

In some embodiments, the statistically based model can be a sub-profile of a plurality of sub-profiles that make up a health profile of the patient.

In some embodiments, the first external device can be the oral appliance holder.

In some embodiments, the record can include a unique identifier that is associated with the patient's master record from a database.

In some embodiments, correlating the record with a patient's master record can include performing an operation to match the unique identifier with the master record and retrieving the patient's master record.

In some embodiments, the record can include values associated with an alert.

In some embodiments, an operation triggered by detection of the alert can be performed.

In some embodiments, the operation can include sending an electronic message associated with the alert to a third-party.

In some embodiments, the electronic message can be sent to the first external device or the second external device.

BRIEF DESCRIPTION OF THE DRAWINGS

For a better understanding of at least certain embodiments, reference will be made to the following Detailed Description, which is to be read in conjunction with the accompanying drawings, wherein.

Figure 1:
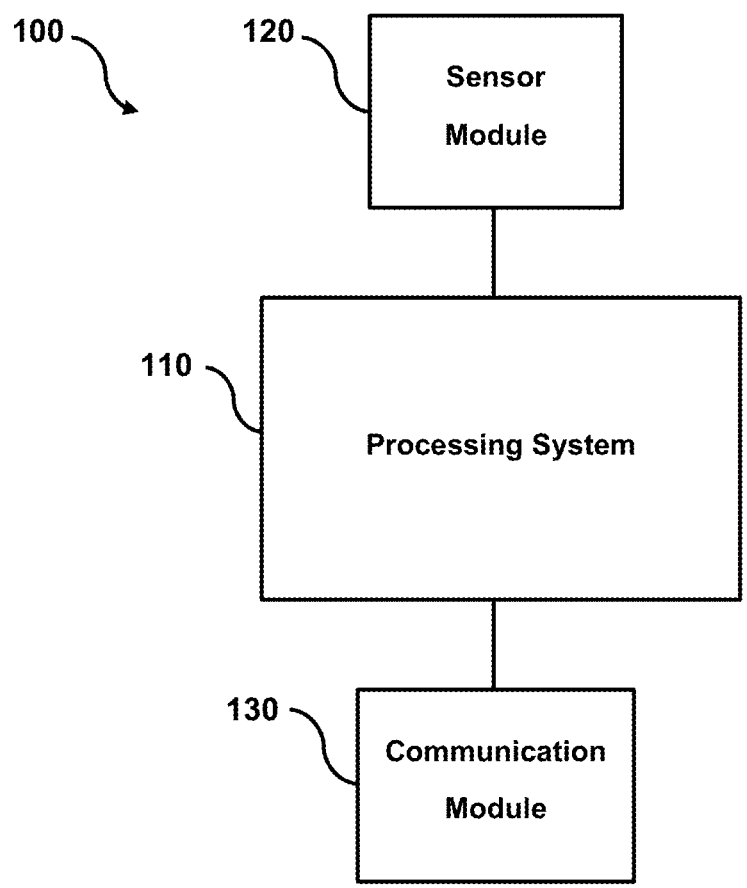
FIG. 1 illustrates a schematic drawing of an appliance holder, according to some embodiments.

The figures depict various embodiments of the present invention for purposes of illustration only, wherein the figures use like reference numerals to identify like elements. One skilled in the art will readily recognize from the following discussion that alternative embodiments of the structures and methods illustrated in the figures can be employed without departing from the principles of the invention described herein.

DETAILED DESCRIPTION

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described. It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order that is logically possible.

FIG. 1 illustrates an embodiment of an appliance holder 100 that can detect the presence or non-presence of an oral appliance, such as an orthodontic appliance (e.g. polymer aligner, polymer retainer) or an appliance constructed in the same manner as a orthodontic appliance but providing no moving or retaining force to the teeth. Appliance holder 100 can include: processing system 110, sensor module 120, and communication module 130. Processing system 110 can include one or more processors that execute various modules. Such modules can be implemented using software or firmware. Alternatively, such modules can be implemented directly as special-purpose hardware. Processing system 110 can include one or more processors, such as low-level processors to handle relatively simple tasks such as sensor monitoring and high-level processors to handle more complex tasks such as data management and communications. These processors can communicate with each other and other components of appliance holder 100 to function as processing system 110. In some embodiments, a low-level processor can be capable of functioning independently of a high-level processor.

Sensor module 120 can detect one or more types of condition associated with appliance holder 100. Sensor module 120 can detect a condition associated with the presence or non-presence of an oral appliance held within the appliance holder, as two examples. Sensor module 120 can continuously or intermittently provide processing system 110 with an indication of the condition. Sensor module 120 can detect a presence or motion within the interior environment of appliance holder 200. Sensor module 120 can include one or more sensors, such as an infra-red, piezo-electric, strain-gauge, hall-effect, capacitive, ultrasonic, microwave, radio (e.g. RFID reader), magnetic, humidity (e.g., capacitive, resistive, or thermal), or optical sensor. In some embodiments, sensor module 120 can include one or more passive infrared (PIR) sensors and/or ultrasonic sensors that receive infrared radiation (or reflected ultrasonic sound) from the ambient environment of the appliance holder. For instance, insertion of an appliance or opening a lid of appliance holder 200 emits infrared radiation which can be detected by sensor module 120. In other embodiments, sensor module 120 can use some other form of sensor than a PIR sensor. In some embodiments, sensor module 120 can include one or more humidity sensors that detect moisture produced by a damp appliance within the ambient environment of the appliance holder. Sensor module 120 can provide an indication to processing system 110 of when motion is present in the ambient environment of appliance holder 200. More generally, sensor module 120 can be a form of sensor that can detect presence of an appliance even if motionless. In some embodiments, sensor module 120 outputs raw data that is analyzed by processing system 110 to determine if motion is present or a user is otherwise present. In some embodiments, motion can be analyzed to determine if it likely corresponds to presence of an appliance or is incidental.

In some embodiments, sensor module 120 can be configured to detect volatilized compounds, i.e. breath odors, emanating from appliances stored within appliance holder 200. Due to the appliance holder having an enclosable small space, volatilized compounds can be captured and detected over an extended period of time. Unlike simpler sensors, such as infrared sensors, with odor sensors compliance can be better tracked because detection of odor can be correlated to drying bacteria of a recently worn aligner. An older aligner left within the case would cause a false positive with regards to compliance using a simple sensor, however this would be avoided using an odor sensor because the older aligner would provide little to no odor, or only odor below a certain threshold. In addition, an odor sensor can be used to track wellness data, which provides additional patient motivation to comply with an aligner protocol or wearing a retainer or similar oral device. In some embodiments, the oral device is constructed in the same manner as an aligner or retainer, e.g., as a clear aligner, but does not adjust or maintain tooth position, but rather is only used by the patient for tracking wellness.

In some embodiments, appliance holder 200 can include a duct and/or fan system to cause volatilized compounds to be deposited onto a sensor. In some embodiments, sensor module 120 can include an electronic nose sensor array, a differential mobility spectrometer, an electrochemical gas sensor, a surface acoustic wave sensor, quartz microbalance sensor, conductive composite, chemiresistor, metal oxide gas sensor and conducting polymer sensor, dye-impregnated polymer film on fiber optic detector, polymer-coated micromirror, an electrochemical gas detector, a chemically sensitive field-effect transistor, carbon black-polymer composite, micro-electro-mechanical system device, and micro-opto-electro-mechanical system device. In some embodiments, sensor module 120 can be configured as an electronic nose and includes of an array of polymer films embedded with conductive or resistive material. When exposed to substance such as a fluid, e.g., a gas, as applied to the present system, the polymer films may swell or contract thereby leading to a change in the DC electrical resistance of the film. The DC resistance across each of the films in the array may be sampled at approximately uniformly-spaced times resulting in a unique signature.

The presence of one or more volatilized compounds can be used to determine the presence of an oral appliance within appliance holder 200. Such volatilized compounds can include analytes deposited on the oral appliances via saliva and directly or indirectly caused by bacteria, viruses, chemical imbalances, dehydration. Such analytes can include organic compounds that can be found in volatilized compounds, which, for example, can include alkanes, alkenes, alkynes, dienes, alicyclic hydrocarbons, arenes, alcohols, ethers, ketones, aldehydes, carbonyls, carbanions, polynuclear aromatics, biomolecules, sugars, isoprenes isoprenoids, volatile organic compounds (VOC), volatile organic analytes (VOA), indoles, skatoles, diamines, pyridines, picolines, an off-gas of a microorganism and fatty acid, pentane, hydrogen sulfide, methyl mercaptan, ammonia, acetone, butane, sulfides, methoxybenzene (anisole), 2-butanone, methyl 2-ethylhexanoate, methyl 2-ethylhexanoate, methyl propionate, 2-pentanone, 3-pentanone, 2,4-dimethyl-1-heptene, methyl isobutyl ketone, 6-methyl-5-hepten-2-one, dimethylsulfoxide, dimethyl sulfide, methyl 2-methylpropionate, 1-ethoxy-2-methylpropane, 1-ethoxy-butane, t-butyl ethyl ether, methyl 2-methyl butanoate, isobutanol, dimethyl sulfide, 2,3-butanedione, 3-hydroxy-2-butanone, butyl acetate, and benzeneacetaldehyde, methanethiol, 2-heptanone, 2-nonanone, and/or 2-undecanone.

Detection and quantification of the odor can also be used to correlate to one or more health conditions of the patient. For example, health conditions such as bad breath, dehydration, diabetes, liver disease, respiratory tract infections, chronic bronchitis, acid reflux, heart disease, gum disease, periodontitis, cancer, infections, pneumonia, ovulation, bacteria presence, and xerostomia. Examples of sensors used to detect airborne analytes that can be attributable to one or more health conditions are described at publications U.S. Pat. No. 6,244,096B1, US20150105683A1, US20040147038A1, U.S. Pat. No. 9,733,226B1, US20060160134A1, US20090247890A1, U.S. Pat. No. 7,977,103B2, US20040236244A1, US20050208614A1, U.S. Pat. No. 6,709,635B1, U.S. Pat. No. 6,575,013B2, U.S. Pat. No. 7,531,137B2, US20090230300A1, US20090230300A1, US20100191474A1, U.S. Pat. No. 8,366,630B2, and U.S. Pat. No. 8,366,630B2, which are incorporated by reference herein.

Processing system 110 can be configured to analyze an amount of time the condition is detected by sensor module 120. Processing system 110 can create a record of the amount of time the condition is detected by sensor module 120. Communication module 130 can be configured to transfer the record to an external device, such as a mobile communication device, remote server, or general-purpose computer. Communication module 130 can be a wired and/or wireless transmission device.

Figure 2:
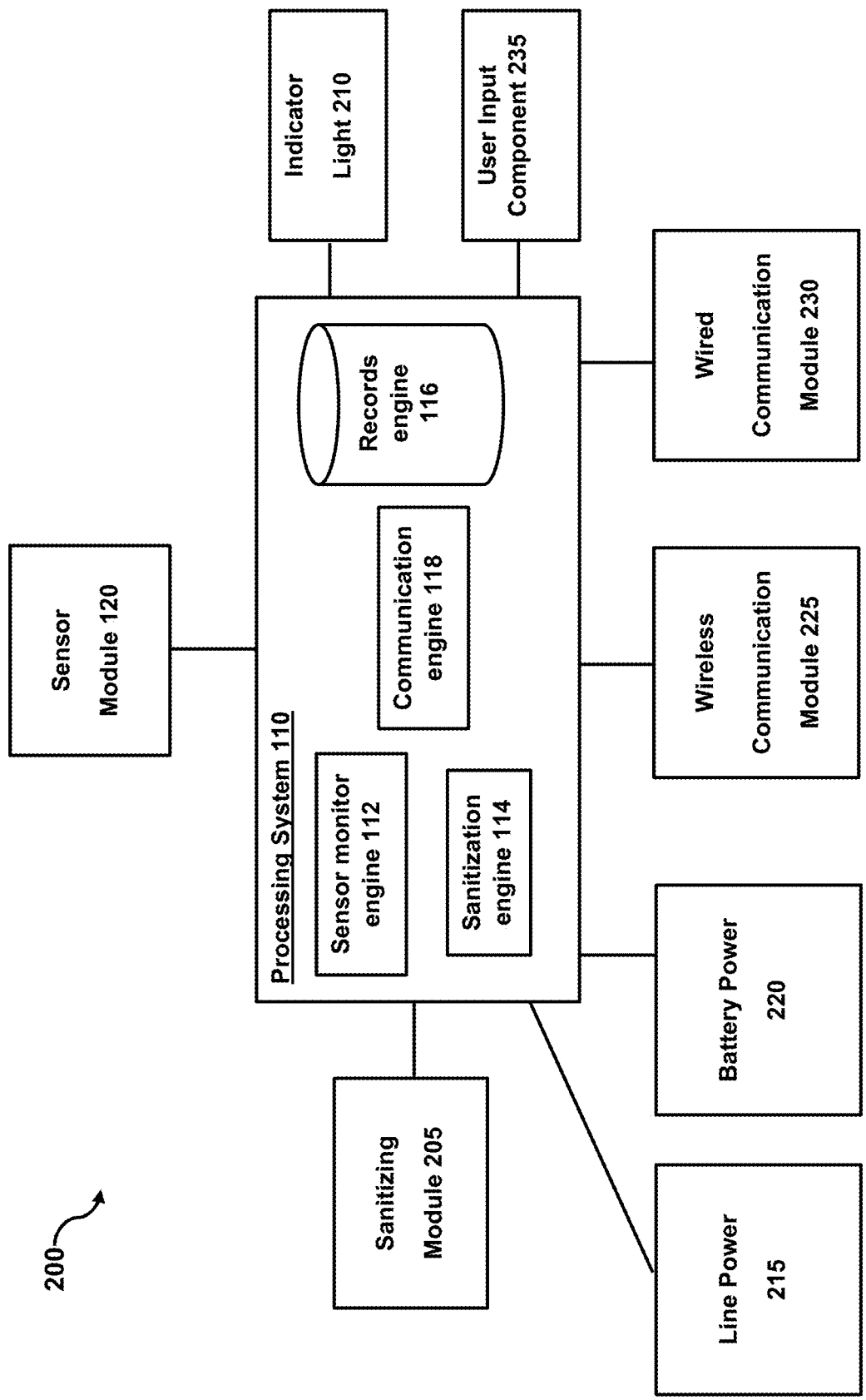
FIG. 2 illustrates a schematic drawing of an appliance holder, according to some embodiments.

FIG. 1 illustrates a simplified embodiment of appliance holder 100. It should be understood that multiple sensors and/or multiple output devices can be optionally present in other embodiments. For example, FIG. 2 illustrates an embodiment of appliance holder 200 that can detect the presence or non-presence of a dental appliance, such as an oral appliance. Appliance holder 200 represents a more detailed embodiment that includes a greater number of optional components and modules. In appliance holder 200, various components can be present including: processing system 110, sensor module 120, indicator light 210, sanitizing module 220, line power source 215, battery-based power source 220, wireless communication module 225, wired communication module 230, and user input component 235.

Processing system 110 of appliance holder 200 can include multiple submodules. Such submodules can be implemented using hardware, firmware, and/or software that is executed by underlying hardware, such as one or more processors. Such modules can include: sensor engine 112, sanitization engine 114, records engine 116, and communications engine 118. For example, such modules can represent code that is executed by a high-level processor and/or a low-level processor of appliance holder 200. Sensor engine 112 can control one or more sensors, for example by activating, deactivating, or regulating power to such sensors. Sensor engine 112 can also receive indications of the condition detected in the appliance holding area of the appliance holder 200 indicating the presence or non-presence of an appliance. In some embodiments, Sensor engine 112 can perform quantitative measurement of one or analytes, such as volatilized compounds. Sensor engine 112 can create time-based records of the indications. Sensor engine 112 can send the records to records engine 116. Records engine 116 can control and include a non-transitory medium, such as flash memory, for storing records received from sensor engine and/or sanitization engine 114. Records engine 116 can be in communication with communication engine 118. Records engine 116 can output records stored in memory to the communication engine 118 based on a signal from communication engine 118.

Sanitizing module 205 can represent a sanitizing device for sanitizing an appliance held by appliance holder 200. Sanitizing module 205 can include am ultraviolet light source or ultrasonic wave inducing transducer. Sanitization engine 114 can control sanitizing module 205 to initiate a sanitization cycle according to a user input, according to a schedule, or by detecting an event, for example, whenever an appliance is placed within appliance holder 200 a sterilization cycle will be initiated. Sanitization engine 114 can output data to records engine 116 for the purpose of creating sanitization records by records engine 116. Sanitization engine 114 can output a signal to indicator light 210 to provide a visual indication to user that the sanitization process is underway or an error has occurred that prevents completion of the sanitization process.

Indicator light 210 can represent a light integrated into appliance holder 200 that outputs light to the external environment around appliance holder 200. Indicator light 210 can be controlled by processing system 110 to indicate to a use of functional status, appliance holder mode, or a wear reminder. Indicator light 210 can include one or more lighting elements, such as light emitting diodes (LEDs). Indicator light 210 can be capable of outputting various illumination modes that can include: multiple colors, multiple animation patterns, and/or such multiple animation patterns at varying speeds. The at least one color, animation pattern, and speed of animation output by indicator light 210 can be determined based on a determination performed by processing system 110. Therefore, based on conditions monitored by processing system 110, indicator light 210 can be illuminated or disabled. When indicator light 210 is illuminated, the one or more colors, animation pattern, and/or speed of the animation output by indicator light 210 can vary based on a determination performed by processing system 110.

Communication engine 118 controls intercommunication between modules of processing system 110. Communication engine 118 also controls wireless communication module 225 and/or wired communication module 230. Wireless communication module 225 and/or wired communication module 230 can allow communication engine 118 to communicate with an external network and/or device. For instance, wireless communication module 225 can communicate with a wireless network that uses the IEEE 802.11a/b/g network protocol standard for communication. Wireless communication module 225 can permit communication engine 118 to communicate with a remote server, which can be maintained by a manufacturer of appliance holder 200 or by a third-party.

The remote server can be configured to provide information to processing system 110 by way of communication engine 118. For example, if one or more modules of processing system 110 require updates, related data can be provided to processing system 110 via wireless communication module 225. Further, communication engine 118 can transmit status information to a remote server, for example information related to data collected by sensor module 120. Such an arrangement can permit an authorized person, such as a care provider, to view information about the use of the appliance holder.

Wireless communication module 225 can permit direct connection with a wireless computerized device, such as a tablet computer or smartphone. In some embodiments, communication is performed via a network connection through a router or other form of direct communication, such as Bluetooth®, Bluetooth LE®, or WiFi Direct®. Once connected, messages can be exchanged between processing system 110 (via wireless communication module 225) and a wireless computerized device, such as to permit an initial configuration of appliance holder 200 to be performed via the computerized wireless device or indirect communication with the remote server. Communication with external devices and/or networks can be intermittent. Hence, when connection with external devices and/or networks is realized, communication engine 118 can communicate to other modules, such as records engine 116, to transmit status and stored records.

User input component 235 can represent a component that receives input that can be passed to processing system 110. User input component 235 can take the form of a button or switch on appliance holder 200. By depressing the button or otherwise actuating user input component 235, a user can provide input via user input component 235 to processing system 110, for example, user input component 235 can be used by a user to initialize a sterilization process by sanitization module 205, reset indicator light 210, or initiate electronic communication with an external device (e.g., initiate wireless discovery mode). Different modes associated with inputs to input component 235 can be initiated according to the length of time input component 235 is activated.

Appliance holder 200 can include battery-based power source 220 and/or line power source 215. Line power source 215 can be used to power appliance holder 200 when such power is available. Line power source 215 can represent a port (e.g., USB port) and a removable wired connection (e.g., USB cable) and/or an inductive charging module that provides DC power from an external source (e.g., AC/DC wall plug, USB port). Line power source 215 can share a common connector (e.g., USB port) with wired communication module 230.

Battery-based power source 220 can include one or more batteries which power the various components of appliance holder 200 when line power source 215 is not available. The batteries can be rechargeable and non-replaceable or be user replaceable. Line power source 215 can provide charging power to batteries of battery power source 220. In some embodiments of appliance holder 200, line power source 215 is not present and/or the appliance holder cannot be capable of connected with line power source 215. Line power source 215 and battery-based power source 220 are illustrated in FIG. 2 as connected with processing system 110. Line power source 215 and battery-based power source 220 are illustrated as only connected with processing system 110, and that line power source 215 and/or battery-based power source 220 can be connected to the various components of appliance holder 200 as necessary to power such components.

Figure 3:
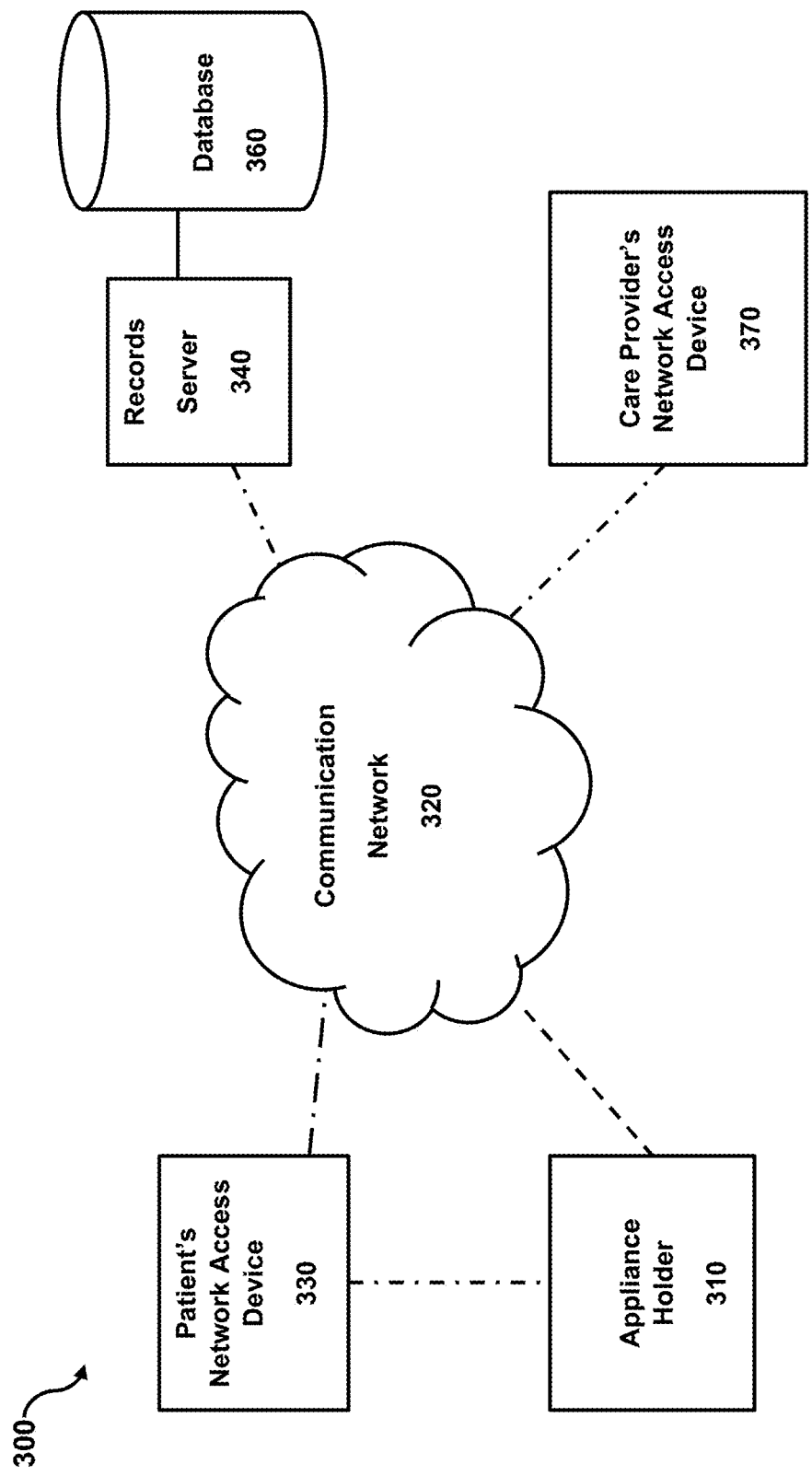
FIG. 3 illustrates a schematic drawing of a network, according to some embodiments.

FIG. 3 illustrates an embodiment of network 300 for facilitating communication of an appliance holder 310 with other devices. Appliance holder 310 can include aspects described with reference to the appliance holders of FIGS. 1 and 2. Appliance holder 310 can communicate with other devices by way of communication network 320, which can include public networks such as the Internet and/or private networks. In some embodiments, appliance holder 310 lacks capability for network communication and therefore transmits information (e.g. wirelessly via Bluetooth®, Bluetooth LE®, or WiFi Direct® connection) through a patient access device 330, such as a smart phone, tablet, or personal computer, that does have network communication capability. In either case, appliance holder 310 directly or indirectly can transfer data records, such as records related to the presence or non-presence of an oral appliance within the holder, to records server 340.

The data sent by appliance holder 310 can be raw data that requires additional processing to create user appliance wear records (e.g., the estimated amount of time the user is using the appliance). Such processing can be, for example, correlating data generated by appliance holder 310 (i.e., time-based data related to detecting presence or non-presence of an oral appliance) to create the wear record. Records server 340 can store such records in database 360. Records server 340 can be configured to provide alerts to care-providers when records correlate with patient non-compliance. Such an alert can be sent to care provider's network access device 370 in the form of an email or other specialized alert. Records server 340 can also be configured to provide wear reminders to patients when records correlate with patient non-compliance. Such a reminder can be sent to patient's network access device 330 in the form of an email, text, and/or or other specialized alert. Such a reminder can additionally or alternatively be sent to appliance holder 310, which can provide a visual alert (e.g., intermittently flashing indicator light 210).

A care provider using network access device 370 can access the records stored on database 360 by communicating with records server 340 through communications network 320. The records can be assigned to a specific patient and formatted for use by a specific application of network access device 370, or alternatively accessible on records server 340 via a web-based application. Based on the records, a care provider can determine whether the user of the appliance associated with appliance holder 310 is wearing the appliance correctly. For example, the appliance can be one of a series of pre-designed oral appliances prescribed for oral treatment of a patient. The series of appliances are designed to incrementally move the teeth from an initial position to a final position to achieve an oral result (e.g., teeth straightening). This is achieved by relatively small movement changes caused by each appliance; hence, it is important for the patient to properly wear each appliance according to a prescribed protocol (e.g., 20 hours/day) to achieve the desired orthodontic result, which non-compliance by the user can negate.

Records that indicate that the appliance is outside of appliance holder 310 for a certain amount of time (e.g., 20-23 hours/day) can be indicative that the patient is complying with the prescribed protocol. This can be verified with in-person examination by the care provider, because such a record can also indicate that the patient is not using appliance holder 310 to store the appliance. If the records correlate with patient compliance, the care provider can adjust the examination follow-up schedule to reduce the number of follow-up examinations required.

Records that indicate that the appliance is outside of appliance holder 310 for a certain amount of time (e.g., 0-19 hours/day) can be indicative that the patient is not complying with the prescribed protocol. Based on interpolating these records, the care provider can contact the patient to investigate whether the patient is not being compliant or whether appliance holder 310 is malfunctioning and sending false records. If an examination indicates that the patient is compliant with the prescribed protocol, then the records do not correlate with non-compliance, which can indicate a fault in appliance holder 310. In such cases, a new appliance holder can be issued to the patient. If records correlate with non-compliance, the prescribed protocol can be adjusted, by for example, rescanning the patient's teeth for a new series of appliances or reverting sequencing back to a prior appliance.

In some embodiments, records server 340 can be configured to receive data regarding the presence/non-presence and/or quantity of one or more types of analytes found in volatilized compounds detected within appliance holder. Such data can be raw data sent by appliance holder 310 and/or processed data from appliance holder 310. In some embodiments, records server 340 can be configured to correlate the processed data with one or more health attributes and maintain a health profile of a patient by updating the health profile with the health attributes. In some embodiments, records server 340 can correlate the processed data with one or more genetic attributes and maintain a health profile of a patient by updating the health profile with the genetic attributes.

Data can be processed by records server 340 to determine the type, presence, relative concentration, ratio, and/or quantity of the one or more analytes, which can function as biomarkers. In some embodiments, a multiplex of analytes can be identified. In some embodiments, records server 340 can be configured to correlate the type, presence, relative concentration, ratio, and/or quantity of one or more analytes to known biomarkers for one or more of a pathology, condition, or health status to determine one or more health attributes. Health attributes can include nutritional information, disease information, hormone information, genetic information, hydration information, PH level information, fluoride information, mineralization information, alcohol information, microbiome information, infectious disease information, cancer information, inflammation information, and/or virus information. Saliva borne biomarkers have been associated with a wide variety of diseases, viral infections, bacterial infections, parasites, physical impairment, inflammation, nutritional imbalances, hormonal imbalances, hormonal levels, menstrual cycles, adrenal disease, diabetes, asthma attacks, cancers, stress, fertility, pregnancy status, sex of a fetus, wellness of a fetus, ovulation status, fertility level, and other wellness issues.

In some embodiments, records server 340 can update the health profile of the patient and compare the most recent data to prior health profiles. In some embodiments, records server 340 can provide statistically weighted statuses and/or predictions of patient wellness based on the health profiles. In some embodiments, alerts for acute indications can be provided to the patient and/or a patient's caregiver so that the patient can seek immediate care. In some embodiments, a patient's health profile can be tracked to provide a life-time view of wellness. Hence, the collected data can provide a better understanding of a patient's health and disease risks, and greater emphasis can be placed on disease prevention and maintaining optimal health for the long term. In some embodiments, lifestyle changes, hormonal, nutritional, dietary, behavioral, and/or therapeutic drug therapies can be recommended by records server 340 based on conditions predicted by the patient's health profile.

In some embodiments, records server 340 can be configured retrieve a patient health profile and update the profile based on the one or more correlated health attributes. In some embodiments, the health profile can be a statistically based model for one or more pathologies. The health profile can be determined by one or more algorithms. The health profile can provide one or more of status, risk, likelihood, tendency, intensity, level, amount, for one or more of the health attributes. The patient health profile can include data regarding past diagnostic tests (e.g. blood/serum tests, salivary tests) records of health events, genetic information, genetic ancestry, psychological information, prescribed drug use, illicit drug use, alcohol use, smoking history, age, weight, race, environmental exposure history, and family health histories. In some embodiments, the patient health profile can be updated in parallel by other sources, for example, by wearable devices that record daily activity, heart rate, etc. In some embodiments, the patient health profile can be updated in parallel by other patient health profiles, which can be anonymized, that share similar genetic profiles, genetic ancestry, live and/or work in the same vicinity, share similar lifestyles, and/or are directly related to the patient. Some or all of these data points can be weighted and considered by system 100 when making conclusions and recommendations based on the detected biomarkers.

In some embodiments, a health profile can made up of several sub-profiles, which are derived from information based on the correlated health attributes. A sub-profile can be a statistically based model for a particular pathology. Each sub-profile can be determined by one or more algorithms. Each sub-profile can provide one or more of status, risk, likelihood, tendency, intensity, level, amount, for a health attribute. Such sub-profiles can include a nutritional profile, disease profile, hormone profile, genetic profile, hydration profile, PH profile, fluoride profile, mineralization profile, alcohol profile, microbiome profile, infectious disease profile, cancer profile, inflammation profile, and/or virus profile.

In some embodiments, records server 340 can be configured for performing predictive analytics to discover new biomarkers, i.e., in order to make statistical determinations on whether a particular analyte, which is not currently determined to be a biomarker, is actually a biomarker in whole or in part for a particular pathology. This can be performed by analyzing data stored in records server 340 of a statistically relevant number of patients with saliva that test positive or negative for the same analyte (e.g., concentration, amount) and have or do not have the same corresponding pathology. This analysis can be supplemented by comparison to additional data, (e.g., lifestyle, genetics, etc.).

Figure 4A:
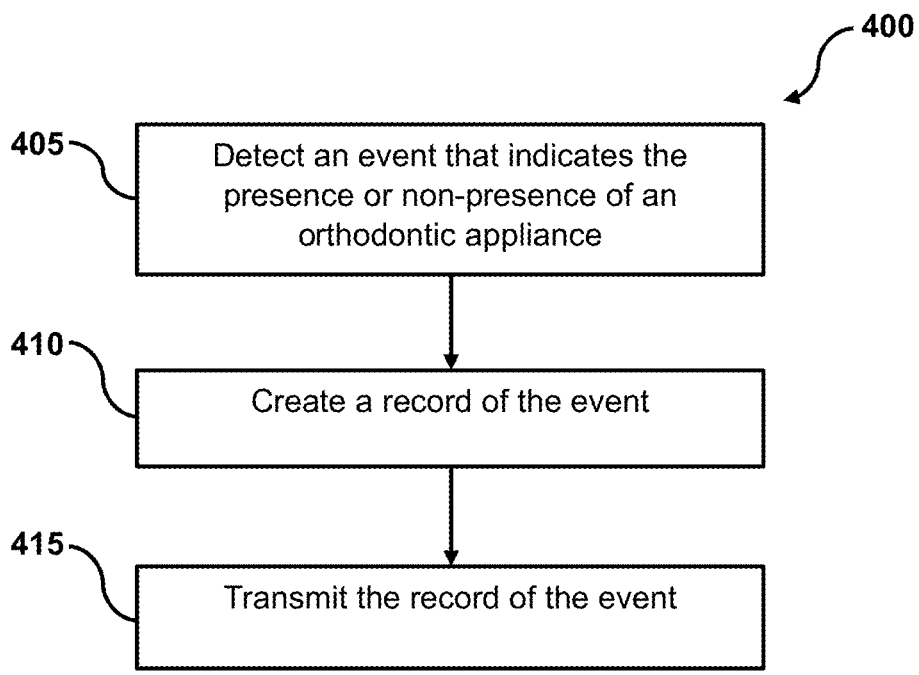
FIGS. 4A and 4B illustrate flow diagrams of methods, according to some embodiments.

Records server 340 can have an AI learning function to perform such discoveries without being commanded to. In some embodiments, this function is performed by a separate bioinformatics engine. Examples of predictive analytics systems and methodology using large data sets are disclosed in U.S. Pat. No. 7,444,308 B2; U.S. Pat. No. 9,679,104 B2; and U.S. Pub. No. 2016/0026917 A1, which are incorporated by reference herein. FIG. 4A illustrates method 400 that can be performed by a processor of an appliance holder, such as any of the appliance holders disclosed herein. Method 400 can be stored as processor executable instructions on a non-transitory medium readable by the processor. The processor can be configured to execute method 400. At operation 405, a processor of an appliance holder detects an event that indicates the presence or non-presence of an oral appliance. For example, sensor module 120 can detect insertion movement or some other physical, electrical, thermal, magnetic, or other measurable property that correlates with presence or non-presence of an appliance within a storage portion of the appliance holder. In some embodiments, the event is a sampling event that occurs according to a predetermined time interval.

At operation 410, the processor creates a record of the event. A sensor of the appliance holder can generate raw data. The decision to process the raw data can be based on the raw data meeting or exceeding a value threshold, which indicates the raw data is useful for creating a record on a non-transitory medium. If the raw data does not meet or exceed the value threshold, no further processing is required, and no record of the event will be created. In some embodiments, the raw data regards the presence/non-presence and/or quantity of one or more types of analytes found in volatilized compounds detected within the appliance holder. The raw data can include a set of data sampled by the sensor according to a predetermined sampling rate, for example, 1 sample per 1-10 seconds or 1-60 minutes. The raw data can be further processed (e.g., to include one or more timestamps) and/or unique identification information to create the record. The raw data can also be incorporated into an existing record (e.g., a daily record) that includes data from events that occurred prior to the event. At operation 415, the processor transmits the record of the event to an external device, such as a smart phone or remote server. Transmission can occur when the processor is connected to the external device by way of a wireless or wired connection. After the record is transmitted, the record can be marked for deletion or overwriting by the processor.

Figure 4B:
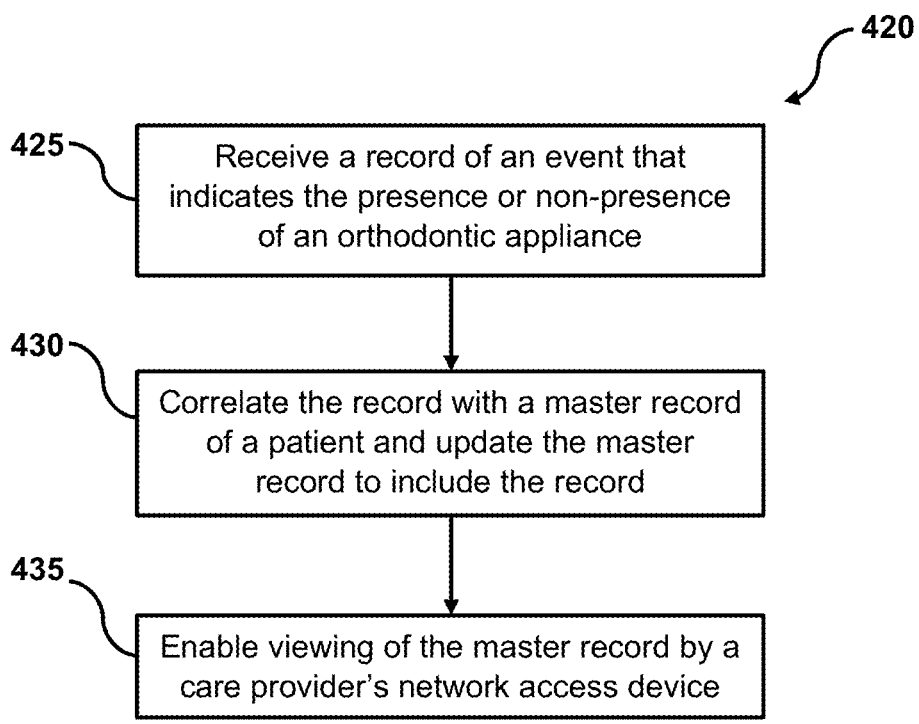

FIG. 4B illustrates method 420 that can be performed by at least one processor of a server that is in direct or indirect communication with an appliance holder, such as any of the appliance holders disclosed herein. Method 420 can be stored as processor executable instructions on a non-transitory medium readable by the processor. The processor can be configured to execute method 420. At operation 425, the processor receives a record that originates from the appliance holder. The record can include a unique identifier that is associated with a particular patient. The record can include data regarding a single event or multiple events that indicated the presence or non-presence of an oral appliance within the appliance holder. The record can include data gathered over a certain period or set of periods, such as several minutes, hours, days, and weeks, i.e., periodical data that can be analyzed for trending information that can provide predication of patient's likelihood of developing some health conditions, which can be used to take action to slow or avoid the illness development. In some embodiments, the record can regard the presence/non-presence and/or quantity of one or more types of analytes found in volatilized compounds detected within appliance holder. In some embodiments, the data is processed to correlate with one or more health attributes. At operation 430, the record can be correlated with a patient's master record by performing an operation to match the unique identifier with the master record. The master record can be retrieved from a database and updated to include the record.

The record can include certain values that are associated with an alert. For example, the values can be associated with compliance or non-compliance with a prescribed appliance wear protocol. In some embodiments, the processor can send a reminder alert to the appliance holder or other device associated with the patient (e.g. smartphone, smartwatch) to remind the patient to wear the appliance. In some embodiments, the processor can send a congratulatory message to the device associated with the patient (e.g. smartphone, smartwatch) to encourage continued compliance with the prescribed appliance wear protocol. In some embodiments, the processor can send an alert to the patient's assigned caregiver that indicates the patient may not be complying with the prescribed appliance wear protocol. In some embodiments, the processor can provide an alert to a health care provider regarding a health related event associated with the correlated health attributes.

In some embodiments, the record includes a patient health profile which can be updated based on the one or more correlated health attributes. In some embodiments, the health profile can be a statistically based model for one or more pathologies. The health profile can be determined by one or more algorithms, which can factor in health attributes collected over weeks, months, and/or years. The health profile can provide one or more of status, risk, likelihood, tendency, intensity, level, amount, for one or more of the health attributes. The patient health profile can include data regarding past diagnostic tests (e.g. blood/serum tests, salivary tests) records of health events, genetic information, genetic ancestry, psychological information, prescribed drug use, illicit drug use, alcohol use, smoking history, age, weight, race, environmental exposure history, and family health histories. In some embodiments, the patient health profile can be updated in parallel by other sources, for example, by wearable devices that record daily activity, heart rate, etc. In some embodiments, the patient health profile can be updated in parallel by other patient health profiles, which can be anonymized, that share similar genetic profiles, genetic ancestry, live and/or work in the same vicinity, share similar lifestyles, and/or are directly related to the patient. Some or all of these data points can be weighted and considered when making conclusions and recommendations based on the detected biomarkers.

In some embodiments, a health profile can made up of several sub-profiles, which are derived from information based on the correlated health attributes. A sub-profile can be a statistically based model for a particular pathology. Each sub-profile can be determined by one or more algorithms. Each sub-profile can provide one or more of status, risk, likelihood, tendency, intensity, level, amount, for a health attribute. Such sub-profiles can include a nutritional profile, disease profile, hormone profile, genetic profile, hydration profile, PH profile, fluoride profile, mineralization profile, alcohol profile, microbiome profile, infectious disease profile, cancer profile, inflammation profile, and/or virus profile.

In some embodiments, predictive analytics can be performed to discover new biomarkers, i.e., in order to make statistical determinations on whether a particular analyte, which is not currently determined to be a biomarker, is actually a biomarker in whole or in part for a particular pathology. This can be performed by analyzing data stored in records of a statistically relevant number of patients with saliva that test positive or negative for the same analyte (e.g., concentration, amount) and have or do not have the same corresponding pathology. This analysis can be supplemented by comparison to additional data, (e.g., lifestyle, genetics, etc.).

At operation 435, the processor enables viewing of all or a portion of the updated master record by the patient's caregiver. Viewing can be enabled by allowing the updated master record to be downloaded by the caregiver's network access device or viewed on a web-based application hosted by the server. In some embodiments, each time the master record is updated or according to a predetermined schedule, the process sends the master record to the caregiver's network access device. In some embodiments, all or portion of the master record can also be made available to the patient's network access device.

Figure 5:
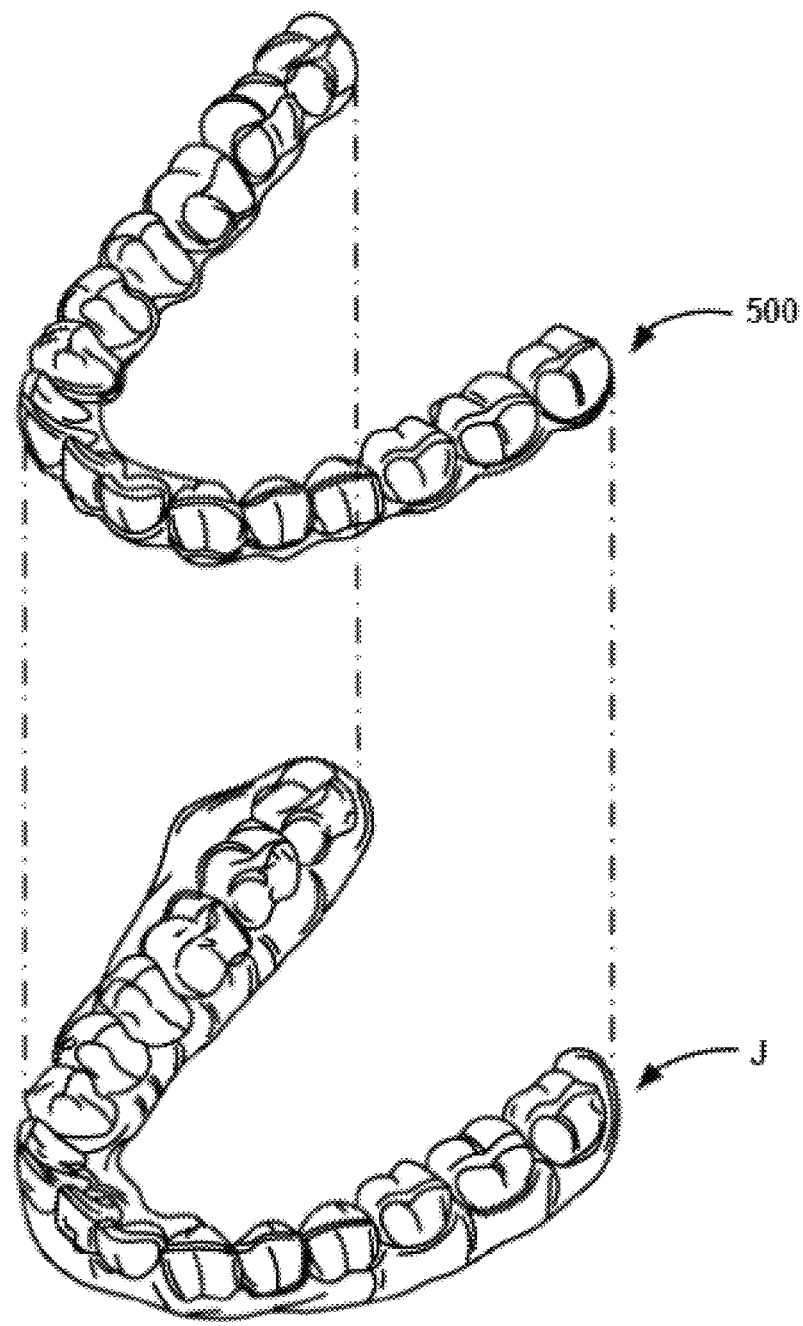
FIG. 5 illustrates an oral appliance, according to some embodiments.

FIG. 5 illustrates oral appliance 500 that can be worn by a patient to achieve an incremental repositioning of individual teeth in jaw J. Oral appliance 500 can include a shell having teeth-receiving cavities that receive and resiliently reposition the teeth. In some embodiments, a polymeric appliance can be formed from a sheet of suitable layers of polymeric material. An appliance can fit over all teeth present in an upper or lower jaw, or less than all of the teeth. In some embodiments, orthodontic appliance 500 can include a feature that helps enable detection by an appliance holder. For example, such a feature can include a material, such as a metal, that can be detected by a metal detecting sensor of the appliance holder. The material can be a metal powder doped into the polymeric material of the appliance or be a discrete piece of metal located at an innocuous portion of the appliance. In some embodiments, the feature is an RFID tag with a unique identifier that can be activated by the appliance.

In some embodiments, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Basic methods for determining an orthodontic treatment plan using a series of incremented appliances as well as instructions for molding oral appliances, are described in U.S. Pat. Nos. 6,450,807, and 5,975,893, which are incorporated by reference herein, but only to an extent that those patents do not contradict the newer teachings disclosed herein.

An appliance can be designed and/or provided as part of a set of a plurality of appliances. In such an embodiment, each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The oral appliances can be generated all at the same stage or in sets or batches, e.g., at the beginning of a stage of the treatment, and the patient wears each appliance until the pressure of each appliance on the teeth can no longer be felt or has resulted in the maximum amount of expressed tooth movement for that given stage. A plurality of different appliances (e.g., set) can be designed and even fabricated prior to the patient wearing any appliance of the plurality. After wearing an appliance for an appropriate period of time, the patient replaces the current appliance with the next appliance in the series until no more appliances remain. The oral appliances are generally not affixed to the teeth and the patient may place and replace the appliances at any time during the procedure (e.g., patient-removable appliances).

The final oral appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Figure 6A:
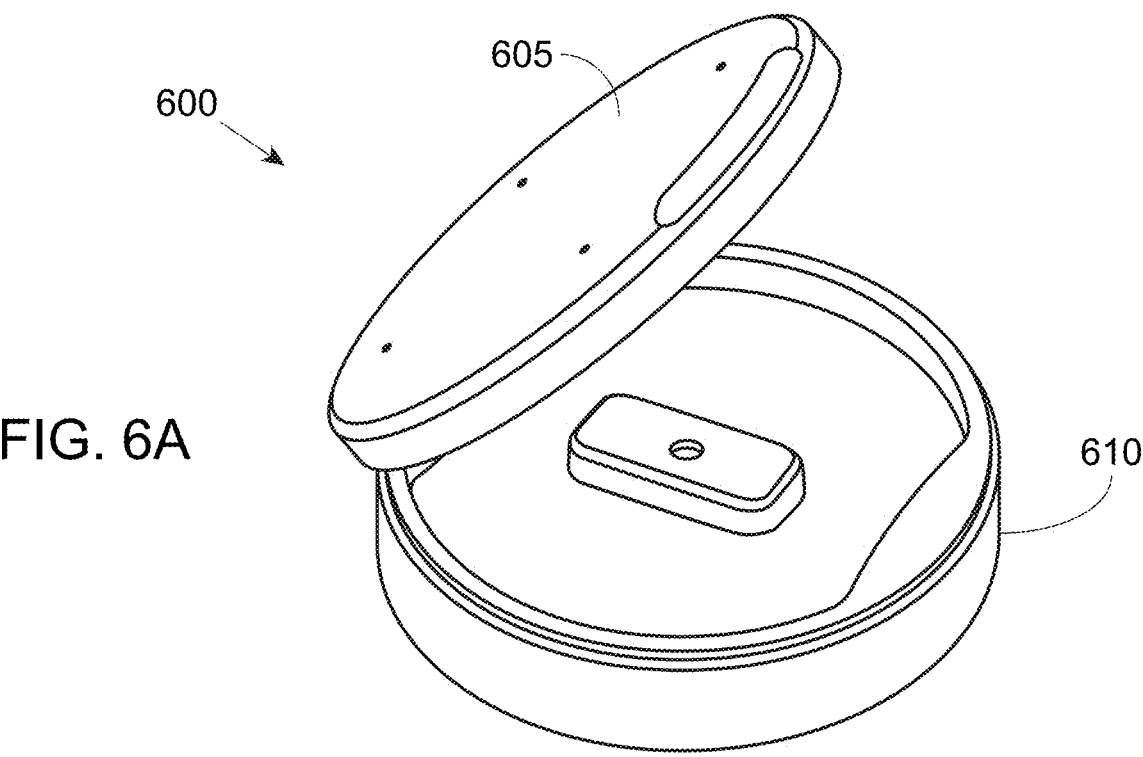
FIGS. 6A-6D illustrate views of an appliance holder, according to some embodiments.
Figure 6B:
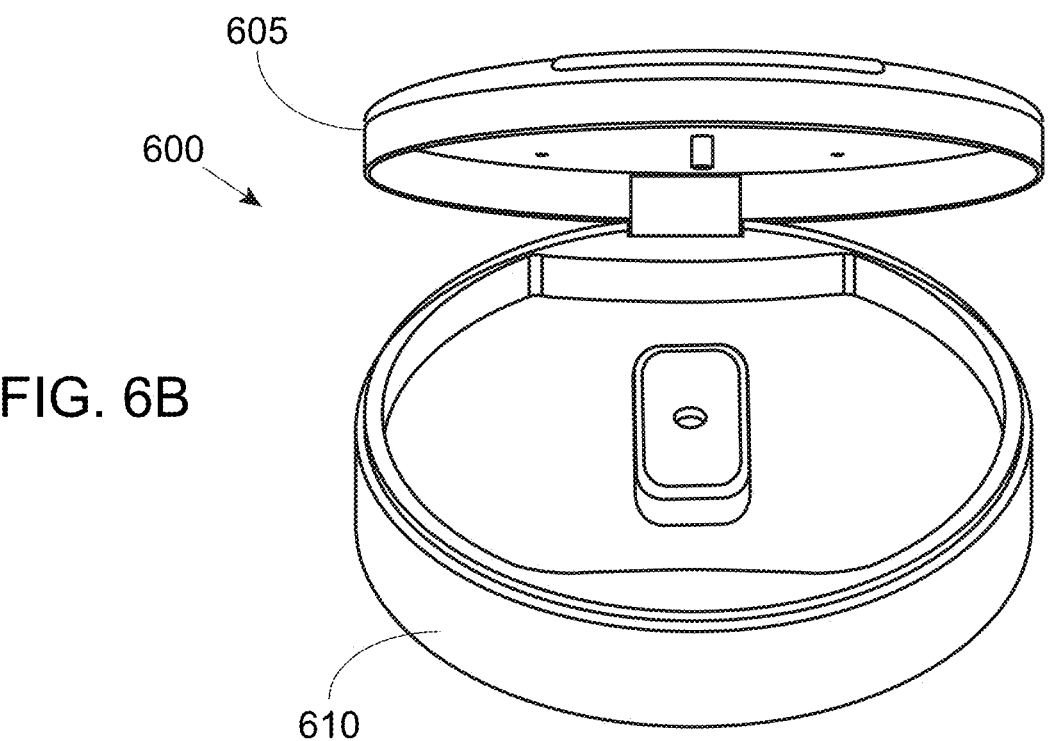

FIGS. 6A and 6B illustrate elevated views of a physical representation of appliance holder 600, which can house the components of any of the appliance holders disclosed herein. Appliance holder 600 includes top lid 605, which can be hinged to bottom housing 610. Top lid 605 and bottom housing 610 can be constructed from a metal or polymer material. Top lid 605 and/or bottom housing 610 are depicted as having a circular shape, but can also have different shapes, such as rectangular.

Figure 6C:
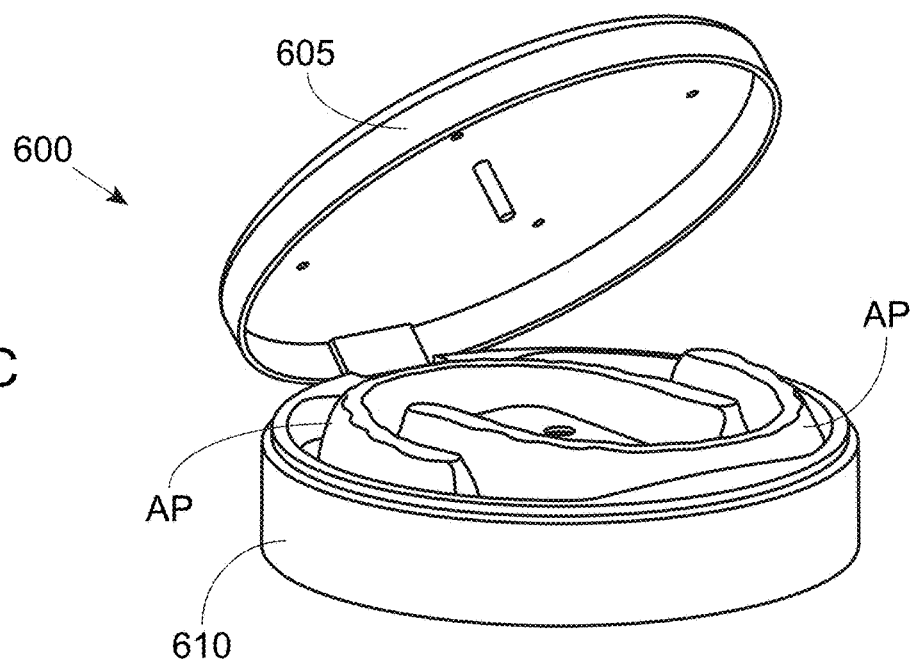
Figure 6D:
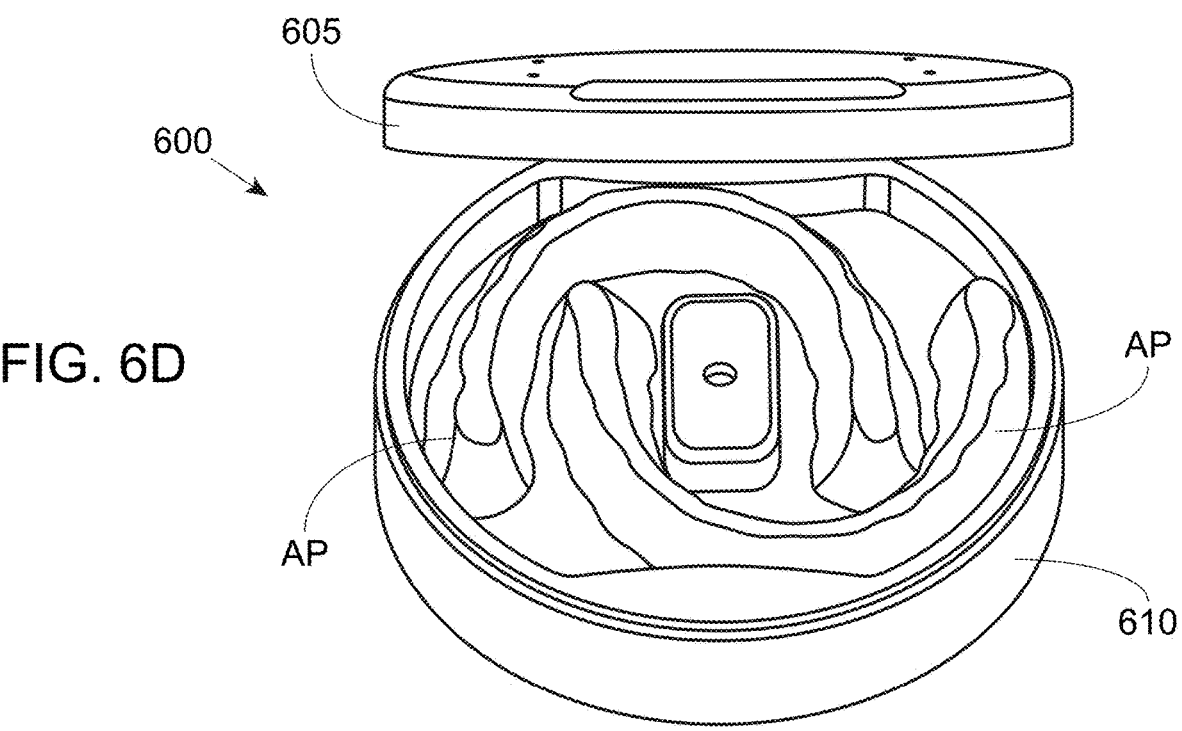

Top lid 605 and/or bottom housing 610 can house numerous components. For example, processing system 110, sensor module 120, indicator light 210, sanitizing module 220, line power source 215, battery-based power source 220, wireless communication module 225, wired communication module 230, and user input component 235 can be stored internally within top lid 605 and/or bottom housing 610. Top lid 605 and/or bottom housing 610 can include features for enabling access to such components, such as battery compartment lids, internal antennas, and communication/line power ports. Top lid 605 and/or bottom housing 610 have interior surfaces that form a cavity for storage of one or more oral appliances, as shown at FIGS. 6C and 6D. Surfaces of the cavity can include sensor ports that enable detection of oral appliances.

Figure 7:
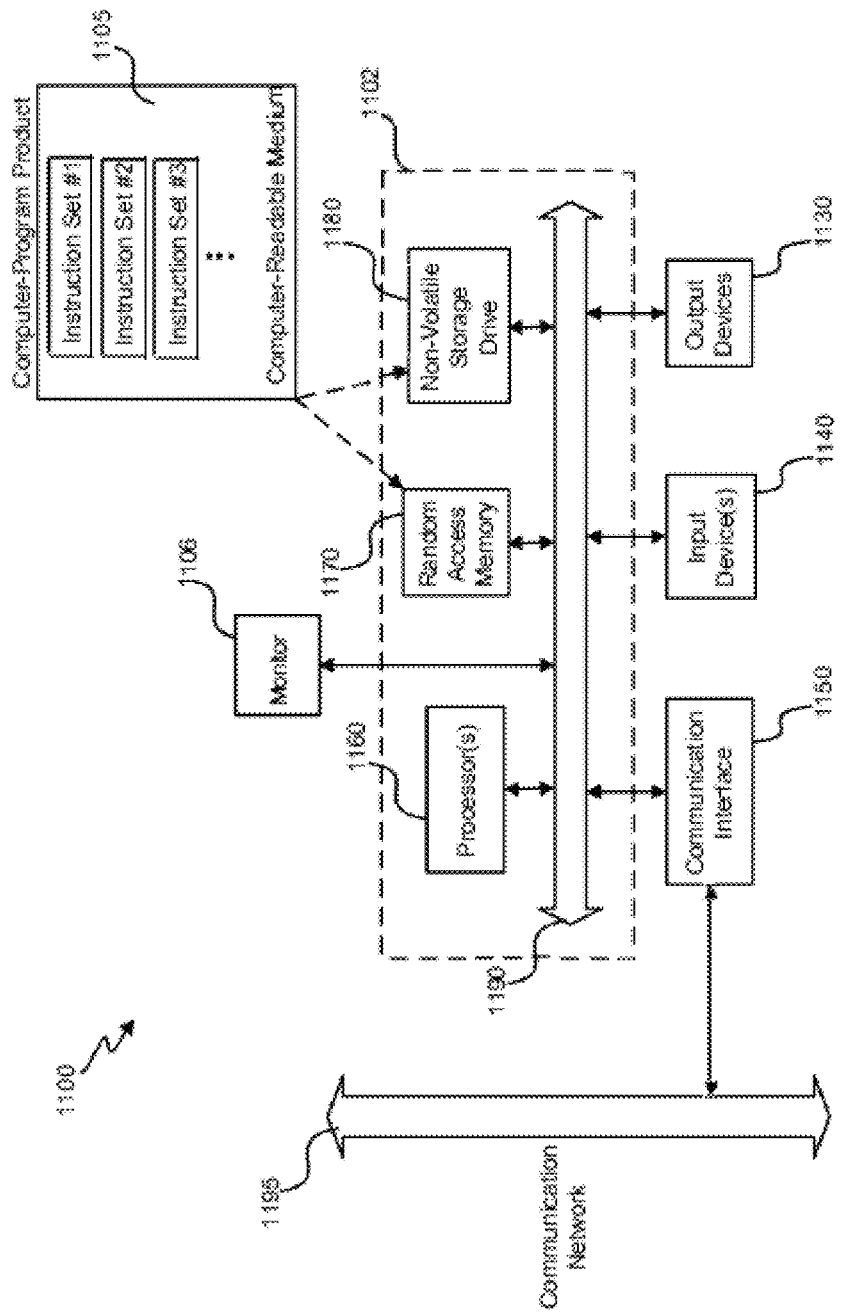
FIG. 7 illustrates a schematic drawing of a computer system, according to some embodiments.

With reference to FIG. 7, an embodiment of a special-purpose computer system 1100 is shown. For example, one or more intelligent components, processing system 110 and components thereof may be a special-purpose computer system 1100. Such a special-purpose computer system 1100 may be incorporated as part of an appliance holder and/or any of the other computerized devices discussed herein, such as a remote server, mobile device, or network. The above methods may be implemented by computer-program products that direct a computer system to perform the actions of the above-described methods and components. Each such computer-program product may comprise sets of instructions (codes) embodied on a computer-readable medium that direct the processor of a computer system to perform corresponding actions. The instructions may be configured to run in sequential order, or in parallel (such as under different processing threads), or in a combination thereof. After loading the computer-program products on a general-purpose computer system 1126, it is transformed into the special-purpose computer system 1100.

Special-purpose computer system 1100 comprises a computer 1102, a monitor 1106 coupled to computer 1102, one or more additional user output devices 1130 (optional) coupled to computer 1102, one or more user input devices 1140 (e.g., keyboard, mouse, track ball, touch screen) coupled to computer 1102, an optional communications interface 1150 coupled to computer 1102, a computer-program product 1105 stored in a tangible computer-readable memory in computer 1102. Computer-program product 1105 directs computer system 1100 to perform the above-described methods. Computer 1102 may include one or more processors 1160 that communicate with a number of peripheral devices via a bus subsystem 1190. These peripheral devices may include user output device(s) 1130, user input device(s) 1140, communications interface 1150, and a storage subsystem, such as random-access memory (RAM) 1170 and non-volatile storage drive 1180 (e.g., disk drive, optical drive, solid state drive), which are forms of tangible computer-readable memory.

Computer-program product 1105 may be stored in non-volatile storage drive 1180 or another computer-readable medium accessible to computer 1102 and loaded into random access memory (RAM) 1170. Each processor 1160 may comprise a microprocessor, such as a microprocessor from Intel® or Advanced Micro Devices, Inc.®, or the like. To support computer-program product 1105, the computer 1102 runs an operating system that handles the communications of computer-program product 1105 with the above-noted components, as well as the communications between the above-noted components in support of the computer-program product 1105. Exemplary operating systems include Windows® or the like from Microsoft Corporation, Solaris® from Sun Microsystems, LINUX, UNIX, and the like. User input devices 1140 include all possible types of devices and mechanisms to input information to computer 1102. These may include a keyboard, a keypad, a mouse, a scanner, a digital drawing pad, a touch screen incorporated into the display, audio input devices such as voice recognition systems, microphones, and other types of input devices. In various embodiments, user input devices 1140 are typically embodied as a computer mouse, a touch screen, wireless remote, a drawing tablet, or a voice command system. User input devices 1140 typically allow a user to select objects, icons, text and the like that appear on the monitor 1106 via a command such as a click of a button or the like. User output devices 1130 include all possible types of devices and mechanisms to output information from computer 1102. These may include a display (e.g., monitor 1106), printers, non-visual displays such as audio output devices, etc. Communications interface 1150 provides an interface to other communication networks, such as communication network 1195, and devices and may serve as an interface to receive data from and transmit data to other systems, WANs and/or the Internet. Embodiments of communications interface 1150 typically include an Ethernet card, a modem (telephone, satellite, cable, ISDN), a (asynchronous) digital subscriber line (DSL) unit, a FireWire® interface, a USBC® interface, a wireless network adapter, and the like. For example, communications interface 1150 may be coupled to a computer network, to a FireWire® bus, or the like. In other embodiments, communications interface 1150 may be physically integrated on the motherboard of computer 1102, and/or may be a software program, or the like.

RAM 1170 and non-volatile storage drive 1180 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1170 and non-volatile storage drive 1180 may be configured to store the basic programming and data constructs that provide the functionality of various embodiments of the present invention, as described above. Software instruction sets that provide the functionality of the present invention may be stored in RAM 1170 and non-volatile storage drive 1180. These instruction sets or code may be executed by the processor(s) 1160. RAM 1170 and non-volatile storage drive 1180 may also provide a repository to store data and data structures used in accordance with the present invention.

RAM 1170 and non-volatile storage drive 1180 may include a number of memories including a main random-access memory (RAM) to store instructions and data during program execution and a read-only memory (ROM) in which fixed instructions are stored. RAM 1170 and non-volatile storage drive 1180 may include a file storage subsystem providing persistent (non-volatile) storage of program and/or data files. RAM 1170 and non-volatile storage drive 1180 may also include removable storage systems, such as removable flash memory. Bus subsystem 1190 provides a mechanism to allow the various components and subsystems of computer 1102 to communicate with each other as intended. Although bus subsystem 1190 is shown schematically as a single bus, alternative embodiments of the bus subsystem may utilize multiple busses or communication paths within the computer 1102.

Throughout the foregoing description, and for the purposes of explanation, numerous specific details are set forth in order to provide a thorough understanding of the described techniques. It will be apparent, however, to one skilled in the art that these techniques can be practiced without some of these specific details. Although various embodiments that incorporate these teachings have been shown and described in detail, those skilled in the art could readily devise many other varied embodiments or mechanisms to incorporate these techniques. Also, embodiments can include various operations as set forth above, fewer operations, or more operations; or operations in an order. Accordingly, the scope and spirit of the invention should be judged in terms of the claims, which follow as well as the legal equivalents thereof.

The invention claimed is:

1. A device for storing an oral appliance, the device comprising:
    an openable container, the openable container having an oral appliance holding portion;
    a processor held within the container;
    a memory module coupled to the processor;
    a communication module coupled to the container; and
    a sensing module comprising an odor snesor and coupled to the appliance holding portion and the processor, the sensing module being configured to generate analyte information, the analyte information being related to presence or non-presence of volatilized compounds emanating from an oral appliance at the appliance holding portion over a period of time, wherein the volatized compounds comprise odors derived from the oral appliance being worn in a patient's mouth;
    wherein the processor is configured to:
    receive the analyte information from the sensing module;
    generate and store use information at the memory module, the use information comprising at least the analyte information and tracking information for a presence of the oral appliance within the appliance holding portion during the period of time based on the detection of the odors by the odor sensor;
    connect the communication module to an external device; and
    transmit the use information to the external device.

2. The device of claim 1, wherein the volatilized compounds comprise one or more of alkanes, alkenes, alkynes, dienes, alicyclic hydrocarbons, arenes, alcohols, ethers, ketones, aldehydes, carbonyls, carbanions, polynuclear aromatics, biomolecules, sugars, isoprenes isoprenoids, VOC, VOA, indoles, skatoles, diamines, pyridines, picolines, an off-gas of a microorganism and fatty acid, pentane, hydrogen sulfide, methyl mercaptan, ammonia, acetone, butane, and sulfides.

3. The device of claim 1, wherein at least one of the processor, memory module, communication module, and sensing module is housed within the bottom housing.

4. The device of claim 1, wherein the communication module is configured to wirelessly communicate with the external device.

5. The device of claim 4, wherein the external device comprises a network access device.

6. The device of claim 5, wherein the network access device is configured to transmit the use information to a remote server.

7. The device of claim 1, further comprising a sanitizing module configured to sanitize the oral appliance at the appliance holding portion.

8. The device of claim 1, wherein the sensing module comprises an electronic nose sensor array.

9. The device of claim 1, wherein the sensor module is configured as an electronic nose and comprises an array of polymer films embedded with conductive or resistive material.

10. A server comprising at least one processor, the at least one processor configured to perform a method comprising:
    receiving a record from a device for storing an oral appliance according to claim 1, the record comprising at least one event that indicates the presence or non-presence of the oral appliance within the device, wherein the at least one event comprises analyte information of volatilized compounds emanating from the oral appliance;
    correlating the record with a patient's master record; and
    updating the patient's master record to include the record.

11. The server of claim 10, wherein the external device comprises a network access device communicatively couplable with the oral appliance holder.

12. The server of claim 10, further comprising correlating the analyte information to at least one health attribute, bodily function, and/or wellness indicator.

13. The server of claim 12, wherein updating the patient's master record comprises correlating analyte information with pre-existing information of the patient's master record to develop a statistically weighted model for the at least one health attribute, bodily function, and/or wellness indicator.

14. The server of claim 13, wherein the statistically based model is a sub-profile of a plurality of sub-profiles that make up a health profile of the patient.

15. The server of claim 10, wherein the record comprises values associated with an alert, the method further comprising performing an operation triggered by detecting the alert.

16. The server of claim 15, wherein the operation comprises sending an electronic message associated with the alert to a third-party.

17. The server of claim 16, wherein the electronic message is sent to the external device.

* * * * *